United States Patent [19]

Ikeda

[11] Patent Number: 5,184,631
[45] Date of Patent: Feb. 9, 1993

[54] DEVICE FOR CLEANING BETWEEN THE TEETH OF ORTHODONTIC PATIENTS

[76] Inventor: Noriko Ikeda, 23-go, 33-banchi, 2-chome, Nishikatae, Jyonan-ku, Fukuoka-city, 812, Japan

[21] Appl. No.: 699,087

[22] Filed: May 13, 1991

[51] Int. Cl.⁵ .............................................. A61C 15/00
[52] U.S. Cl. ......................................... 132/323; 433/3
[58] Field of Search ..................... 433/3; 132/323, 324, 132/325, 326, 327

[56] References Cited

U.S. PATENT DOCUMENTS

| 677,947 | 7/1901 | Cowan | 132/324 |
| 922,824 | 5/1909 | Tubbs | 132/325 |
| 1,220,409 | 3/1917 | Freschl | 132/324 |
| 4,280,518 | 7/1981 | Gambaro | 132/323 |
| 4,531,530 | 7/1985 | Aiken | 132/323 |

Primary Examiner—Cary E. O'Connor
Attorney, Agent, or Firm—Jordan and Hamburg

[57] ABSTRACT

A device for cleaning teeth of orthodontic patients wearing orthodontic braces having a wire element extending between the braces includes an elongated member having an end portion formed with a filament support, a filament carried by the filament support, and a hook formed on the member and operable to be hooked onto the wire while the elongated member is manually manipulated to cause the filament to clean the teeth of the orthodontic patient.

8 Claims, 3 Drawing Sheets

DEVICE FOR CLEANING BETWEEN THE TEETH OF ORTHODONTIC PATIENTS

BACKGROUND OF THE INVENTION

The present invention relates to a device for cleaning between teeth undergoing orthodontic treatment wherein braces are attached to the labial side surface of the teeth and a wire extends between the braces. The device of the present invention cleans food particles from between the teeth and the wire and also removes plaque adhering to the teeth.

When performing dental orthodontic, braces are respectively bonded onto the surfaces of each tooth to be straightened, and these braces are connected by a wire to straighten the teeth.

However, when cleaning the teeth with a toothbrush during several years of orthodontic treatment, the tips of the bristles of a toothbrush are unable to enter into the spaces between the teeth sufficiently because of the presence of the mounted wire, making it difficult to remove food particles and plaque in the spaces between the teeth.

Dental floss has been used for the purpose of removing food particles and plaque remaining between the teeth. Dental floss removes food particles and plaque while passing a thread between adjoining tooth surfaces, but during orthodontic treatment the wire becomes an obstacle that prevents this function from being carried out.

SUMMARY OF THE INVENTION

An object of the present invention is to provide a device which is operable to overcome the disadvantages of the prior art and which is operable to clean between the teeth to remove food particles and plaque even though braces and a wire are mounted on the teeth for effecting orthodontic treatment.

The present invention includes a device for cleaning between the teeth of orthodontic patients and includes a device having a filament-stretching space at an end portion of an elastic rod element and a filament in the filament-stretching space. The device also has a hook to hook onto the orthodontic wire extending between the teeth. As the device is hooked onto the wire by the hook, the patient can manually manipulate the device as the stretched filament cleans the teeth.

DESCRIPTION OF PREFERRED EMBODIMENTS

Figure 1:
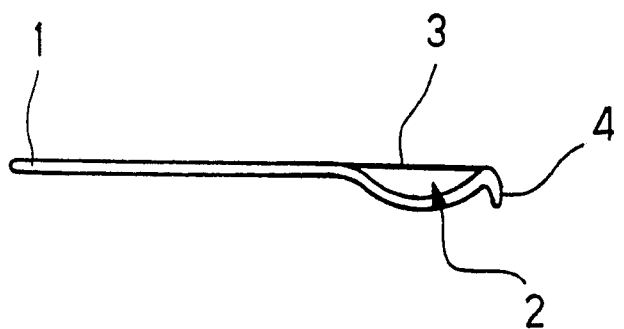
FIG. 1 is an elevational view of a device for cleaning between the teeth according to a first embodiment of the present invention.

FIG. 1 is an elevational view of a device for cleaning between the teeth according to a first embodiment of the present invention. In FIG. 1 a rod-shaped member 1 made from synthetic resin material such as plastic has an end portion with a curved shape to form a filament-stretching space 2. A filament 3 is stretched between both ends of the filamentstretching space 2. Also a hook 4 is formed by a bend at the end of the member 1.

Figure 2:
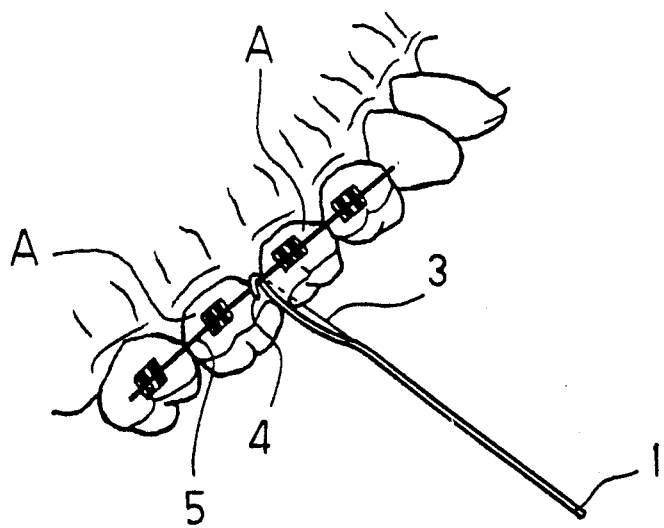
FIG. 2 is an explanatory view showing use of the device shown in FIG. 1.

FIG. 2 is an explanatory view showing use of the device of FIG. 1. By inserting the hook portion 4 in the space between wire 5 and the buccal surfaces of teeth A and A, it is possible to insert filament 3 stretched in the filament-stretching space 2 between the adjoining surfaces of teeth A and A, thereby making it possible to remove food particles and plaque without difficulty by a forward and backward movement.

Figure 3:
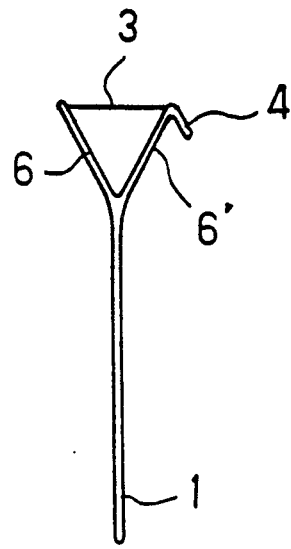
FIG. 3 is an elevational view of a device for cleaning between the teeth according to a second embodiment of the present invention.

FIG. 3 is a view of a second embodiment in which a filament-stretching space 2 is formed by forks 6 and 6' on the end of rod-shaped member 1 formed from a synthetic resin material such as plastic. A filament 3 is stretched between the ends of the forks 6 and 6', and the end of fork 6' has a hook 4.

Figure 4:
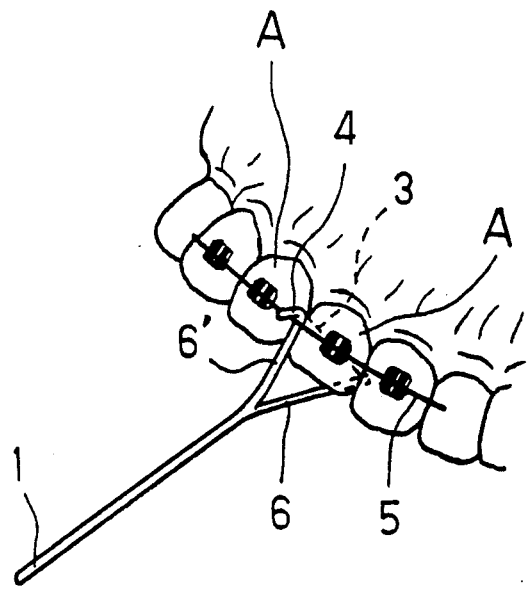
FIG. 4 is an explanatory view showing use of the device of FIG. 3.

FIG. 4 is an explanatory view showing use of the device of FIG. 3, wherein the hook 4 is inserted between wire 5 and labial surfaces of anterior teeth A and A making it possible, to insert the filament 3 between the adjoining surfaces of anterior teeth A and A, so that by moving the device 1 up and down parallel to the longitudinal axis of the teeth, it is possible to remove food particles and plaque without difficulty.

Figure 5:
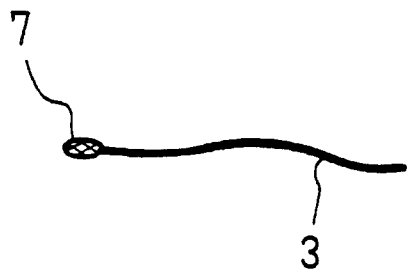
FIG. 5 is an elevational view of a device for cleaning between the teeth according to a third embodiment of the present invention.

FIG. 5 is a view of a device for cleaning between teeth according to a third embodiment in which one end of a filament 3 is connected to an enlarged end portion 7 formed from synthetic resin material such as plastic, and the other end is in an explanatory free state.

Figure 6:
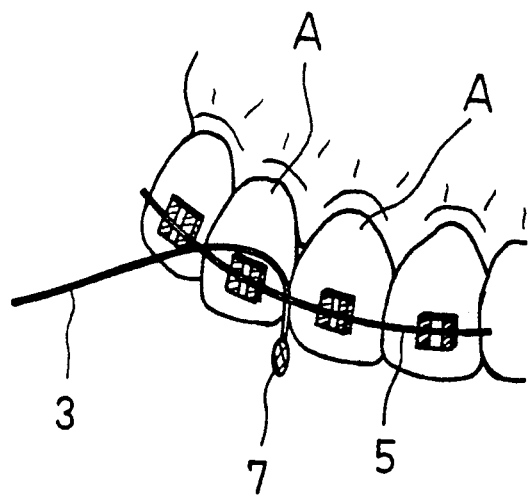
FIG. 6 is an explanatory view showing use of the device of FIG. 5.

FIG. 6 is a view showing use of the device of FIG. 5, wherein the head portion 7 is inserted from above (in the case of the upper teeth) into the space between wire 5 and the buccal surface and labial surface of teeth A and A, so that food particles and plaque can be removed easily by rubbing back and forth with the head portion 7 while the free end of filament 3 is being gripped.

The device for cleaning between teeth of the present invention as explained above can easily advance the filament between adjoining surfaces of the teeth by inserting the guide portion or the guide piece into the space between the wire and the teeth without hindrance from the wire used for orthodontic treatment, making it possible to remove food particles and plaque without difficulty by back and forth or up and down movements.

Although the present invention has been fully described by way of example with reference to the accompanying drawings, it is to be understood that various changes and modifications will be apparent to those skilled in the art. Therefore, unless otherwise such changes and modifications depart from the scope of the invention, they should be construed as being included therein.

What I claim is:

1. The combination comprising:
   (a) orthodontic braces for use on teeth of an orthodontic patient;
   (b) said orthodontic braces comprising an orthodontic wire which extends between the teeth of an orthodontic patient wearing said orthodontic braces;
(c) cleaning means for cleaning the teeth of said orthodontic patient; said cleaning means comprising:
(c-1) an elongated member having an end portion formed with filament support means for supporting a filament;
(c-2) an orthodontic wire-engaging means on said filament support means;
(d) said orthodontic wire-engaging means comprising a hook hookable onto said orthodontic wire while said elongated member is manually manipulated to cause said filament to clean the teeth of said orthodontic patient.

2. The combination according to claim 1, wherein said elongated member has a handle section which is grasped by said orthodontic patient to effect said manual manipulation, said hook having a generally V-shaped configuration.

3. The combination according to claim 2, wherein said handle section has a longitudinal axis which is co-axial with said stretched filament.

4. The combination according to claim 2, wherein said filament support means comprises a bow-shaped part having an arcuate section terminating at two spaced ends, said filament extending between said two spaced ends, said hook being integrally formed at one of said two spaced ends.

5. The combination according to claim 4, wherein said bow-shaped part has a convex side and an opposite concave side, said hook being formed by two converging leg parts, one of said leg parts being formed by a portion of said convex side of said bow-shaped part, the other of said leg parts being formed by a projection which projects from said convex side of said bow-shaped part.

6. The combination according to claim 2, wherein said filament support means comprises two leg parts each having one end extending from said handle section and each having an opposite end spaced from one another, said filament extending between said spaced opposite ends, said hook being formed on one of said leg parts, said hook being formed by two converging hook sections, one of said hook sections being formed by a portion of said one leg part, the other of said hook sections being formed by a projection which projects away from said one leg part.

7. A method of self-cleaning of teeth of orthodontic patients wearing orthodontic braces which include a wire element extending between the teeth comprising the steps of:
providing an elongated member having an end portion supporting a stretched filament and also having an integral hook;
hooking said hook on said wire element;
manually manipulating and moving said elongated member while maintaining said hook hooked to said wire element; and
cleaning said teeth with said stretched filament during said manipulating step and during said step of maintaining said hook hooked to said wire element.

8. A method of self-cleaning of teeth of an orthodontic patient wearing orthodontic braces which include an orthodontic wire element extending between the teeth comprising the steps of:
providing an elongated cleaning member having an end portion supporting a stretched filament and an elongated handle portion co-axial with said stretched filament;
providing a wire-engaging hook on said end portion juxtaposed to one end of said stretched filament;
hooking said hook onto a portion of said orthodontic wire element which extends between said two teeth; and
manipulating said elongated cleaning member such that said stretched filament cleans between said two teeth.

* * * * *